US00PP19127P2

(12) United States Plant Patent
Kleinhanns

(10) Patent No.: US PP19,127 P2
(45) Date of Patent: Aug. 19, 2008

(54) ***OSTEOSPERMUM* PLANT NAMED 'ASTRA CANDY SPOON'**

(50) Latin Name: *Osteospermum hybrida*
Varietal Denomination: Astra Candy Spoon

(75) Inventor: Christoph E. Kleinhanns, Gernrode (DE)

(73) Assignee: Hamer Bloemzaden B.V., H. I. Ambacht (NL)

( * ) Notice: Subject to any disclaimer, the term of this patent is extended or adjusted under 35 U.S.C. 154(b) by 0 days.

(21) Appl. No.: 11/827,392

(22) Filed: Jul. 11, 2007

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

PP14,316 P2 * 11/2003 Sorensen ..... Plt./360

* cited by examiner

*Primary Examiner*—Wendy C. Haas
(74) *Attorney, Agent, or Firm*—Jondle & Associates, P.C.

(57) ABSTRACT

A *Osteospermum* cultivar particularly distinguished by pink flowers with spoon-shaped petals, early flowering, good garden performance and a compact plant habit is disclosed.

1 Drawing Sheet

Genus and species: *Osteospermum hybrida.*
Variety denomination: 'Astra Candy Spoon'.

BACKGROUND OF THE NEW PLANT

The present invention comprises a new and distinct cultivar of *osteospermum,* botanically known as *Osteospermum hybrida,* and hereinafter referred to by the cultivar name 'Astra Candy Spoon'. 'Astra Candy Spoon' originated from a polycross breeding system in March 2003 in Quedlinburg, Germany. The female parent was an *osteospermum* plant with purple spoon flowers.

The new cultivar was first propagated in summer of 2006 from mother stock and has been asexually reproduced through vegetative cuttings for four generations. The present invention has been found to retain its distinctive characteristics.

SUMMARY OF THE INVENTION

The following are the most outstanding and distinguishing characteristics of this new cultivar when grown under normal horticultural practices in Quedlinburg, Germany.

1. Pink flowers with spoon shaped petals;
2. Early flowering;
3. Good garden performance; and
4. Compact plant habit.

DESCRIPTION OF THE PHOTOGRAPH

This new *Osteospermum* plant is illustrated by the accompanying photograph which shows the overall plant habit, including blooms, buds and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Astra Candy Spoon'. The data which defines these characteristics were collected from asexual reproductions carried out in Quedlinburg, Sachsen-Anhalt, Germany. Data was collected. Color references are primarily to the R.H.S. Colour Chart of The Royal Horticultural Society of London (R.H.S.) ($4^{th}$ ed).

DETAILED BOTANICAL DESCRIPTION

Classification:
- *Family.*—Compositae.
- *Botanical.*—*Osteospermum hybrida.*

Parentage:
- *Female parent.*—*Osteospermum* plant with purple spoon flowers.
- *Male parent.*—Unknown; crossing done by bees.

Plant:
- *Form and habit.*—Upright, bushy.
- *Growth and branching habit.*—Compact upright growing, basal branching.
- *Height.*—40.0 cm to 50.0 cm.
- *Width.*—Radius: 25.0 cm to 35.0 cm. Diameter: 50.0 cm to 70.0 cm.
- *Propagation.*—Terminal tip cuttings.
- *Time to produce a finished flowering plant.*—10 to 12 weeks.
- *Time to initiate and develop roots.*—4 to 6 weeks.
- *Root description.*—Fine rooting system with white to light brown roots.

Leaves:
- *Arrangement.*—Spiral.
- *Shape.*—Rough.
- *Apex.*—Spiky.
- *Base.*—Longish running to the stem.
- *Margin.*—Weak ridged.

*Immature leaf.*—General color: RHS 135B (Dark green). Upper surface: RHS 137C (Dark green). Lower surface: RHS 137D (Lighter dark-green).
*Mature leaf.*—General color: RHS 132A (Dark green). Upper surface: RHS 137A (Dark green). Lower surface: RHS 137B (Lighter dark-green).
*Length.*—5.0 cm to 7.5 cm.
*Width.*—1.5 cm to 3.0 cm.
*Texture.*—Rough.
*Petioles.*—Petioles winged by the leaf nearly direct to the branches.

Stems:
*Total number of branches.*—30 to 50.
*Length.*—40.0 cm to 50.0 cm.
*Diameter.*—Radius: 0.1 cm to 0.3 cm. Diameter: 0.2 cm to 0.6 cm.
*Internode length.*—1.0 cm to 4.0 cm.
*Color.*—RHS 137C (Green with some anthocyanin).
*Texture.*—Smooth.

Inflorescence buds:
*Shape.*—Oval to longish.
*Length.*—0.5 cm to 1.0 cm.
*Diameter.*—Radius: 0.3 cm to 0.5 cm. Diameter: 0.6 cm to 1.0 cm.
*Color.*—RHS 137D (Light green) with small amount of violet in the middle.

Inflorescence:
*Type.*—Small flower (Astra) spoon type.
*Blooming habit* (*flowering season*).—May to November.
*Quantity of inflorescences per plant.*—40 to 80.
*Lastingness of the inflorescences on the plant.*—About 7 days, but very much dependent on irrigation, fertilizer and temperature.
*Fragrance.*—Soft.
*Inflorescence diameter.*—Radius: 1.5 cm to 3.0 cm. Diameter: 3.0 cm to 6.0 cm.
*Disc diameter.*—Radius: 0.3 cm to 0.6 cm. Diameter: 0.6 cm to 1.2 cm.

Disc floret:
*Quantity per inflorescence.*—50 to 70.
*Shape.*—Tubular.
*Tube color* (*closed*).—RHS 83A (Dark-violet but getting darker to the tip), lower part RHS 141D (Light green).
*Tube color* (*mature*).—RHS 83A (Dark-violet but getting darker to the tip), lower part RHS 141D (Light green).
*Length.*—0.6 cm to 1.0 cm.
*Diameter* (*at apex*).—Radius: Less than 0.1 cm. Diameter: 0.1 cm.
*Apex.*—Relatively flat.
*Apex color.*—RHS 83A (Dark violet).
*Base.*—RHS 143B (Soft green).
*Margin.*—Fused until about 0.3 cm before apex.

Ray floret:
*Quantity per inflorescence.*—15.
*Shape.*—Longish, in the middle folded to tube.
*Color.*—RHS 70B (Light pink to pink). Upper surface: RHS 65B (Light pink to pink). Lower surface: RHS 91D (Light-violet).
*Length.*—2.0 cm to 3.0 cm.
*Width.*—0.2 to 0.7 cm.
*Apex.*—RHS92A (Light violet), nearly round, a little bit ridged.
*Base.*—Fused.
*Margin.*—Entire.
*Texture.*—Smooth.
*Peduncle.*—Length: 1.0 cm to 2.0 cm. Diameter: Radius: 2.0 cm to 3.0 cm. Diameter: 4.0 cm to 6.0 cm. Texture: Soft. Color: RHS 65B (Pink).

Phyllaries:
*Arrangement.*—Not fused.
*Quantity.*—15.
*Shape.*—Longish.
*Color.*—RHS 143C (Light green). Upper surface: RHS 143C (Light green). Lower surface: RHS 143B (Darker green).
*Length.*—0.6 cm to 1.3 cm.
*Width.*—0.1 cm to 0.3 cm.
*Apex.*—Very spiky.
*Base.*—Running broad into the flowerbase.
*Margin.*—Lower part nearly transparent, at the tip RHS 143A (Green).
*Texture.*—Rough, pubescent.

Reproductive organs:
*Androecium.*—Location: Ray florets and disc florets. Stamens: Quantity: 5. Shape: Longish. Color: RHS 83A (Dark-violet). Filament length: 0.2 cm to 0.3 cm. Filament diameter: Radius: Less than 0.1 cm. Diameter: Less than 0.1 cm. Anther: Shape: Longish. Color: RHS 83A (Dark-violet). Length: 0.1 cm to 0.3 cm. Diameter: Radius: Less than 0.1 cm. Diameter: Less than 0.1 cm. Pollen: Color: RHS 25A (Bright-orange). Amount: Moderate.
*Gynoecium.*—Location: Disc florets. Pistils: Number: 1. Length: 0.5 cm to 0.8 cm. Diameter: Radius: Less than 0.1 cm. Diameter: Less than 0.1 cm. Stigma: Color: RHS N89C (Dark-violet). Shape: Round. Length: Less than 0.1 cm. Diameter: Radius: Less than 0.1 cm. Diameter: Less than 0.1 cm. Style: Color: RHS 155B (Nearly white). Length: 0.5 cm to 0.7 cm. Diameter: Radius: 0.1 cm. Diameter: 0.1 cm. Shape: Cylindrical.

Seeds:
*Color.*—RHS 165A (Brown).
*Length.*—0.4 cm to 0.7 cm.
*Diameter.*—Radius: 0.1 cm to 0.2 cm. Diameter: 0.2 cm to 0.4 cm.
*Shape.*—Triangular to flat.

Disease and insect resistance: Resistance and susceptibility is typical of the species.

COMPARISON WITH KNOWN CULTIVARS

'Astra Candy Spoon' differs from the female parent plant in that the female parent's growth habit is not as compact as that of 'Astra Candy Spoon'. Additionally, the female parent of 'Astra Candy Spoon' has bigger flowers and the "spoon form" is not as distinct as that of 'Astra Candy Spoon'.

The male parent is not known for 'Astra Candy Spoon'. Crossing was done by bees.

'Astra Candy Spoon' differs from the commercial *Osteospermum* plant named 'Aknik' (U.S. Plant Pat. No. 14,316) in that 'Astra Candy Spoon' has a middle ray floret ring that is light pink, while 'Aknik' has a middle ray floret ring that is violet blue. Additionally, 'Astra Candy Spoon' has smaller flowers than that of 'Aknik'.

I claim:

1. A new and distinct cultivar of *Osteospermum* plant as described and shown herein.

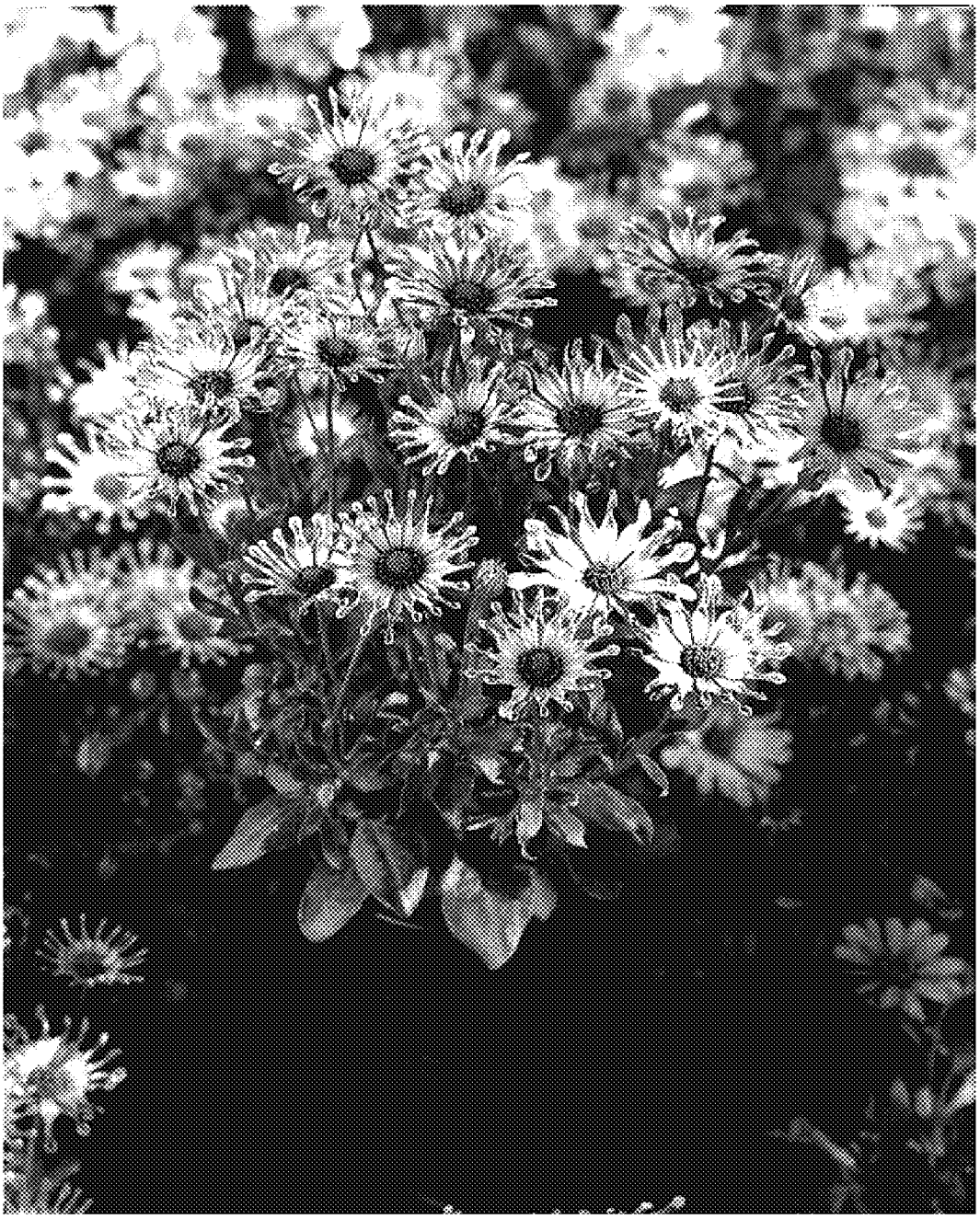

* * * * *